US006679899B2

(12) United States Patent
Wiener et al.

(10) Patent No.: US 6,679,899 B2
(45) Date of Patent: Jan. 20, 2004

(54) METHOD FOR DETECTING TRANSVERSE VIBRATIONS IN AN ULTRASONIC HAND PIECE

(75) Inventors: Eitan T. Wiener, Cincinnati, OH (US); William T. Donofrio, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 180 days.

(21) Appl. No.: 09/953,006

(22) Filed: Sep. 14, 2001

(65) Prior Publication Data

US 2002/0052616 A1 May 2, 2002

Related U.S. Application Data

(60) Provisional application No. 60/242,251, filed on Oct. 20, 2000.

(51) Int. Cl.$^7$ ................................................ A61B 17/32
(52) U.S. Cl. ........................................ 606/169; 604/22
(58) Field of Search .................... 606/166, 169, 606/170, 171, 176, 177, 178, 179; 604/22

(56) References Cited

U.S. PATENT DOCUMENTS

| | | | |
|---|---|---|---|
| 2,917,691 A | 12/1959 | DePrisco et al. | 318/118 |
| 4,425,115 A | 1/1984 | Wuchinich | 604/22 |
| 5,001,649 A | 3/1991 | Lo et al. | 364/484 |
| 5,026,387 A * | 6/1991 | Thomas | 606/169 |
| 5,062,827 A | 11/1991 | Wiksell | 604/22 |
| 5,112,300 A | 5/1992 | Ureche | 604/22 |
| 5,180,363 A | 1/1993 | Idemoto et al. | 202/32 |
| 5,400,267 A | 3/1995 | Denen et al. | 364/552 |
| 5,425,704 A | 6/1995 | Sakurai et al. | 604/22 |
| 5,449,370 A | 9/1995 | Vaitekunas | 606/169 |
| 5,630,420 A | 5/1997 | Vaitekunas | 128/662.03 |
| 5,707,369 A | 1/1998 | Vaitekunas et al. | 606/31 |
| 5,873,873 A * | 2/1999 | Smith et al. | 606/1 |
| 5,879,364 A | 3/1999 | Bromfield et al. | 606/169 |

(List continued on next page.)

FOREIGN PATENT DOCUMENTS

| | | | |
|---|---|---|---|
| EP | 1025806 A1 | 8/2000 | A61B 17/32 |
| JP | 2000-175926 | 6/2000 | |

OTHER PUBLICATIONS

European Search Report dated Feb. 15, 2002.

*Primary Examiner*—Michael J. Milano
*Assistant Examiner*—Victor Nguyen

(57) ABSTRACT

A method for detecting transverse mode vibrations in an ultrasonic hand piece/blade is achieved by monitoring the power delivered to the hand piece/blade to determine whether it increases as expected when power levels applied to the hand piece/blade are changed. While the blade is being held in midair, the power delivered to the hand piece/blade and/or the impedance of the hand piece/blade is measured at a first power level. Using the value obtained at the first power level, the expected power at a second power level is calculated and used to set a pass/fail threshold level for an actual measured power. Alternatively, the threshold is set for the impedance is set. Next, the actual power delivered to the hand piece/blade and/or the impedance of the hand piece/blade is measured at a level 5 power setting. A determination is made whether the hand piece/blade exhibits transverse mode behavior based on whether the actual measured power exceeds the established pass/fail threshold level. If this is the case, operation of the generator is inhibited, a "Transverse Mode Vibrations Present in Hand Piece/Blade" error code is stored in the generator, and a "Bad Hand Piece" message is displayed on a liquid crystal display on the generator. In addition, a method for detecting transverse mode vibration in an ultrasonic hand piece/blade is achieved by monitoring power delivered to the hand piece/blade to determine if the an extraordinary power increase occurs as the drive frequency is shifted downward and/or upward from a primary intended resonance operating frequency.

19 Claims, 15 Drawing Sheets

U.S. PATENT DOCUMENTS

| | | | |
|---|---|---|---|
| 5,935,143 A * | 8/1999 | Hood | 606/169 |
| 5,944,737 A * | 8/1999 | Tsonton et al. | 606/205 |
| 5,968,007 A | 10/1999 | Simon et al. | 604/22 |
| 5,989,275 A | 11/1999 | Estabrook et al. | 606/169 |
| 6,017,354 A | 1/2000 | Culp et al. | 606/170 |
| 6,019,775 A | 2/2000 | Sakurai | 606/169 |
| 6,066,135 A | 5/2000 | Honda | 606/39 |
| 6,068,647 A * | 5/2000 | Witt et al. | 606/205 |
| 6,090,123 A | 7/2000 | Culp et al. | 606/180 |
| 6,387,109 B1 * | 5/2002 | Davison et al. | 606/169 |
| 6,432,118 B1 * | 8/2002 | Messerly | 606/169 |

* cited by examiner

FIG. 4

| POWER LEVEL | PEAK | RMS |
|---|---|---|
| Small Signal & Diagnostics | 141mA | 100mA |
| LEVEL 1 | 282mA | 200mA |
| LEVEL 2 | 353mA | 250mA |
| LEVEL 3 | 423mA | 300mA |
| LEVEL 4 | 494mA | 350mA |
| LEVEL 5 | 564mA | 425mA |

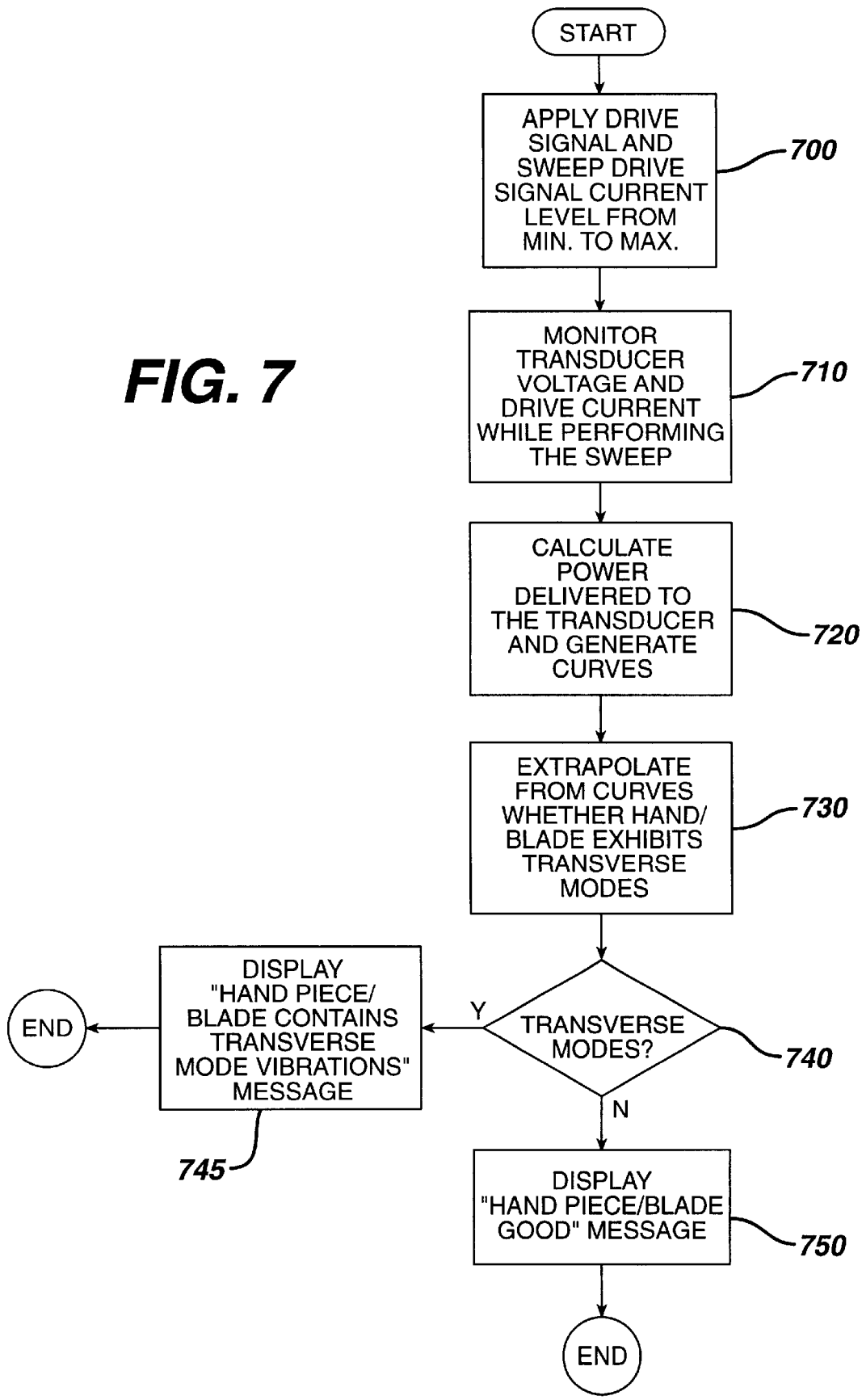

| Generator Power level | Current [mA] | Impedance [Ohms] | Power [Watts] |
|---|---|---|---|
| 1 | 200 | 50 | 2 |
| 2 | 250 | 50 | 3.125 |
| 3 | 300 | 50 | 4.5 |
| 4 | 350 | 50 | 6.125 |
| 5 | 400 | 50 | 8 |

| Generator Power level | Current [mA] | Impedance [Ohms] | Power [Watts] |
|---|---|---|---|
| 1 | 200 | 50 | 2 |
| 2 | 250 | 50 | 3.125 |
| 3 | 300 | 60 | 5.4 |
| 4 | 350 | 70 | 8.575 |
| 5 | 400 | 90 | 14.4 |

METHOD FOR DETECTING TRANSVERSE VIBRATIONS IN AN ULTRASONIC HAND PIECE

RELATED APPLICATIONS

The present invention relates to, and claims priority of, U.S. Provisional Patent Application Serial No. 60/242,251 filed on Oct. 20, 2000, having the same title as the present invention, which is incorporated herein by reference.

BACKGROUND OF THE INVENTION

1. Field of the Invention

The invention generally relates to ultrasonic surgical systems and, more particularly, to a method for detecting transverse mode vibrations in an ultrasonic hand piece/blade.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat, as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop (that includes a voltage controlled oscillator, a frequency divider, a power switch, a matching network and a phase detector), stabilizes the frequency applied to the hand piece. A microprocessor controls the amount of power by sampling the frequency, current and voltage applied to the hand piece, because these parameters change with load on the blade.

The power versus load curve in a generator in a typical ultrasonic surgical system, such as that described in the Thomas patent, has two segments. The first segment has a positive slope of increasing power as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, continues to monitor the transducer current to voltage phase angle, and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot: (i) hop over other resonance modes or make any heuristic decisions, such as what resonance to skip or lock onto, and (ii) ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Some limited diagnostic tests performed in the past involve sending a signal to the transducer to cause the blade to move and the system to be brought into resonance or some other vibration mode. The response of the blade is then determined by measuring the electrical signal supplied to the transducer when the system is in one of these modes. The ultrasonic system described in U.S. Application Ser. No. 09/693,621, filed on Oct. 20, 2000, which is incorporated herein by reference, possesses the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art ultrasonic systems.

Another problem associated with the prior art ultrasonic systems is unwanted vibrations in the hand piece/blade. Ultrasonic blades also vibrate along an axis which is perpendicular to the longitudinal axis of vibration of the hand piece/blade. Such vibrations are called transverse mode vibrations. If the longitudinal vibration is considered to be in the Z direction in an X, Y, Z coordinate system, vibrations along a Y-axis of the blade are called transverse "flap mode" vibrations and vibrations along an X-axis of the blade are called transverse "hook mode" vibrations. Blades typically have a sheath surrounding their blade part.

Transverse mode vibrations generate heat, which leads to high blade and/or blade sheath temperatures. This can damage tissue surrounding an indented narrow cut or coagulation zone, thus adversely affecting patient healing and recovery time. In addition, transverse mode vibrations can cause blade tip failures. The vibrations may also be indicative of defects in the hand piece, such as damaged transducer disks. While excess transverse mode vibrations are sometimes annoyingly audible, often a user will ignore them for as long as possible. It is therefore advantageous to detect transverse mode vibrations to prevent undesired effects, such as tissue damage which can occur from an over heated blade.

SUMMARY OF THE INVENTION

The invention is a method for detecting transverse mode vibrations in an ultrasonic transducer/blade. With this method, the power delivered to the hand piece/blade is monitored at multiple power levels to determine whether it changes as expected when the power levels applied to the hand piece/blade are changed. (Power levels are associated with specific currents at which the generator drives the hand piece/blade, regardless of load changes on the blade.)

Transverse mode vibrations are excited by (non-linear) interactions of longitudinal vibrations with the hand piece/blade. These vibrations bend the blade, thereby causing the generation of heat, which drains energy from the desired longitudinal vibrations. This energy drain manifests itself as an increase in hand piece/blade impedance, thereby necessitating an increase in the power delivered to the hand piece/blade to maintain the required current through the transducer of the hand piece.

The non-linear mechanical coupling of energy from longitudinal to transverse vibrations is appreciable only above certain energy/displacement thresholds. Therefore, if the impedance seen at a low "reference" power level is less than the impedance of the same hand piece/blade at a higher power level, then transverse vibrations are more than likely present. In embodiments, a power measurement at a low power level under test is used to calculate an expected power at a high power level.

A reference power consumption measurement at a low power level setting is performed. This measurement is used to establish pass/fail power consumption levels for a high power level setting. The reference power level measurement is essential, because the transducer/blade impedance seen by the generator depends on the blade used.

In accordance with the invention, while the blade is being held in midair, the power delivered to the hand piece/blade is measured at a low power level setting, where the drive current is low and does not trigger transverse vibrations. Using the value obtained at the low drive current level setting, the expected power at a second high power is calculated and used to set a pass/fail threshold for a second measurement at the high power level setting. Next, the actual power delivered to the hand piece/blade is measured at the high power level setting, and a determination is made whether the hand piece/blade exhibits transverse mode vibrations based on whether the actual measured power at the high power level setting exceeded the established pass/fail threshold level. If this is the case, operation of the generator is inhibited, a "Transverse Mode Vibrations Present in Hand Piece/Blade" error code is stored in the generator, and a "Bad Hand Piece" message is displayed on the LCD of the console.

In accordance with an embodiment, while the blade is being held in midair, the drive current level is swept from a minimum drive current to a maximum drive current. During the current sweep, the transducer voltage and current drive signals are monitored and stored in non-volatile memory located in the generator. Using the stored voltage and current data, the power delivered to the transducer is calculated, and the Power-Delivered vs. Drive Current and Hand Piece/Blade Impedance vs. Drive Current response curves are generated. Using the generated response curves, an extrapolation is performed to determine whether the Hand Piece/Blade exhibits transverse mode vibrations. If this is the case, operation of the generator is inhibited, a "Transverse Mode Vibrations Present in Hand Piece/Blade" error code is stored in the generator, and a "Bad Hand Piece" message is displayed on the LCD of the console.

In an alternative embodiment, a Multiple Level Drive Power vs. Power Delivered relationship and/or a Multiple Level Drive Power vs. Impedance relationship is used to detect or predict potential transverse mode problems, along with an "over-drive" of the hand piece at one or several power drive levels beyond the normal range of power levels used. These "over-drive" power levels are particularly effective at rapidly identifying problematic or potentially problematic transverse mode conditions.

In another embodiment, the power delivered to the hand piece is measured at multiple frequencies while a high power drive signal is applied to the hand piece. Alternatively, an "over-drive" is used. Here, three frequencies, i.e., a first frequency, a second frequency and a third frequency, are measured in close proximity to each other. The first frequency is the primary resonance frequency, otherwise referred to as the main or intended longitudinal resonance frequency of the hand piece/blade. The second frequency is slightly below the first frequency. The third frequency is slightly above the first frequency. The expected impedance or power increases somewhat at both the second and third frequencies. If the impedance or power is substantially higher or higher than expected, this condition indicates the presence of a transverse resonance, which may create undesired heat and/or reduce ultrasonic energy delivered into tissue. In this case, an alert or alarm is generated by the generator console. If necessary, a handicap limited functionality or complete disabling of the hand piece drive is performed.

Instead of monitoring impedance or power delivered to the hand piece, other variables can be monitored for comparison, such as the phase, the current, the voltage, a power factor, or the like. Alternately, rather than comparing the primary frequency measurements to both a slightly higher and a slightly lower frequency measurement, the comparison is performed at only the "second frequency" or at only the "third frequency." As a result, the monitoring process is accelerated in cases where monitoring additional frequencies is not necessary or needed.

In another embodiment of the invention, while the blade is being held in midair or on tissue, the power delivered to the hand piece/blade is measured at first and second frequencies. Using the values obtained at the first and second frequencies, the expected power at a third frequency, a fourth frequency and a fifth frequency are calculated and used to set a pass/fail threshold level for an actual measured third power through an actual measured fifth power, respectively. Next, the actual power delivered to the hand piece/blade is measured at the third, fourth, and fifth frequencies. A determination is made whether the hand piece/blade exhibits transverse mode vibration based on whether any of the actual measured powers exceed the established pass/fail threshold levels. If this is the case, operation of the generator is inhibited, and an alarm/alert message and/or audible alarm/alert is generated. Rather than monitoring the power delivered to the hand piece, in alternative embodiments other variables are monitored for comparison purposes, such as the phase, the impedance, the current, the voltage, the power factor, the phase margin, or the like.

In a further embodiment of the invention, the occurrence of whether a transverse frequency is located near the intended drive resonance is determined, and difficulties associated with the detection of transverse modes stimulated by the primary/main resonance drive frequency at high power are resolved.

The method provides an indication of whether a hand piece, which failed the power level tests, will exhibit transverse vibrational modes if it is used. In addition, the method eliminates the need to know the specific type of blade being used with the hand piece during diagnostic testing.

BRIEF DESCRIPTION OF THE DRAWINGS

The foregoing and other advantages and features of the invention will become more apparent from the detailed description of the preferred embodiments of the invention given below with reference to the accompanying drawings in which:

FIG. 4 is a table showing the maximum current setting associated with various power levels at which the hand piece is driven;

FIG. 7 is a flowchart illustrating an alternative embodiment of the invention;

DETAILED DESCRIPTION OF THE PREFERRED EMBODIMENTS

Figure 1:
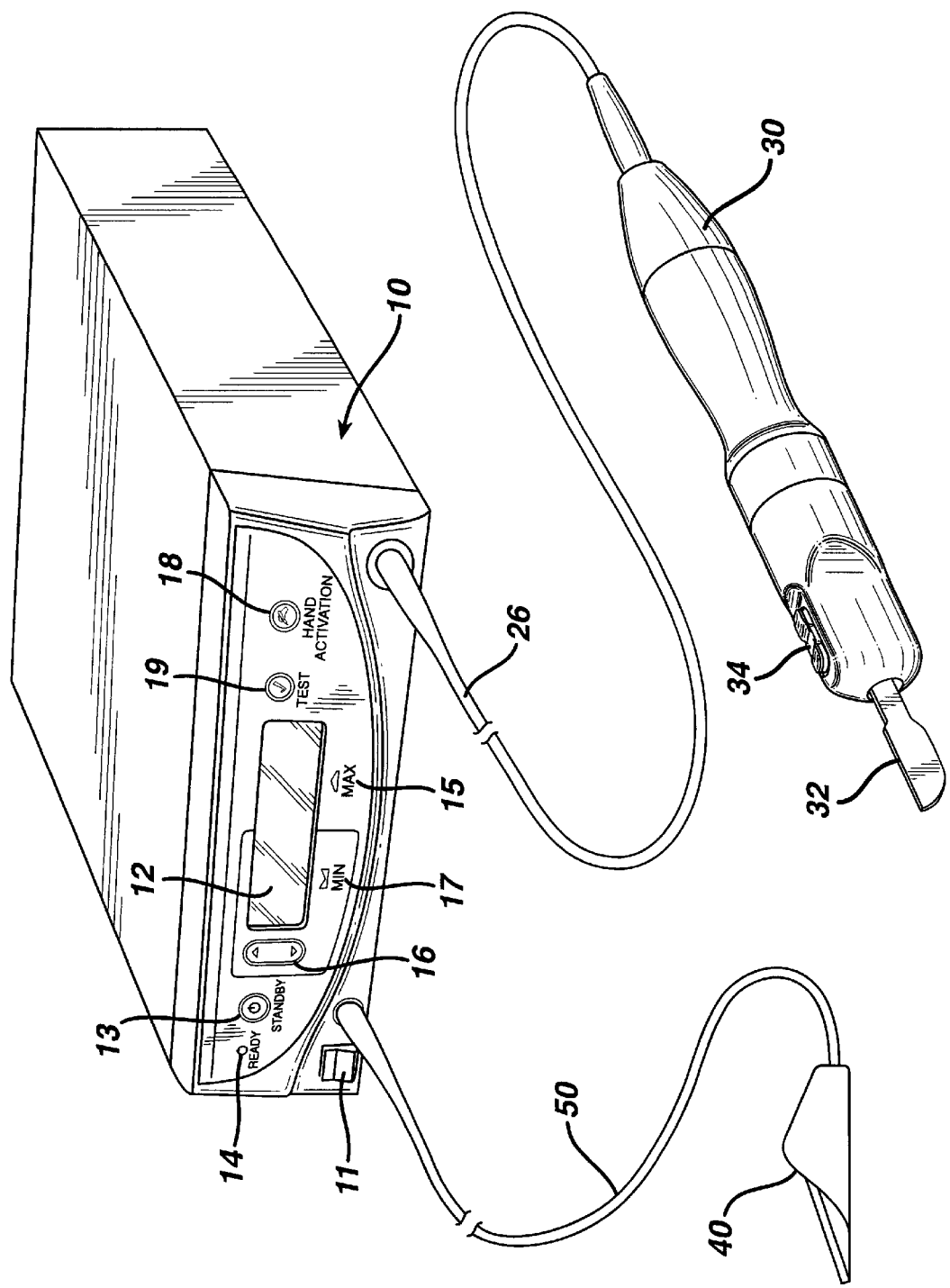
FIG. 1 is an illustration of a console for an ultrasonic surgical cutting and hemostasis system, as well as a hand piece and foot switch in which the method of the present invention is implemented.

FIG. 1 is an illustration of a system for implementing the method in accordance with the invention. By means of a first set of wires in cable 20, electrical energy, i.e., drive current, is sent from the console 10 to a hand piece 30 where it imparts ultrasonic longitudinal movement to a surgical device, such as a sharp scalpel blade 32. This blade can be used for simultaneous dissection and cauterization of tissue. The supply of ultrasonic current to the hand piece 30 may be under the control of a switch 34 located on the hand piece, which is connected to the generator in console 10 via wires in cable 20. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is to supply maximum power, the MAX button 15 is depressed. If a lesser power is desired, the MIN button 17 is activated. The level of power when MIN is active is set by button 16.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Figure 2:
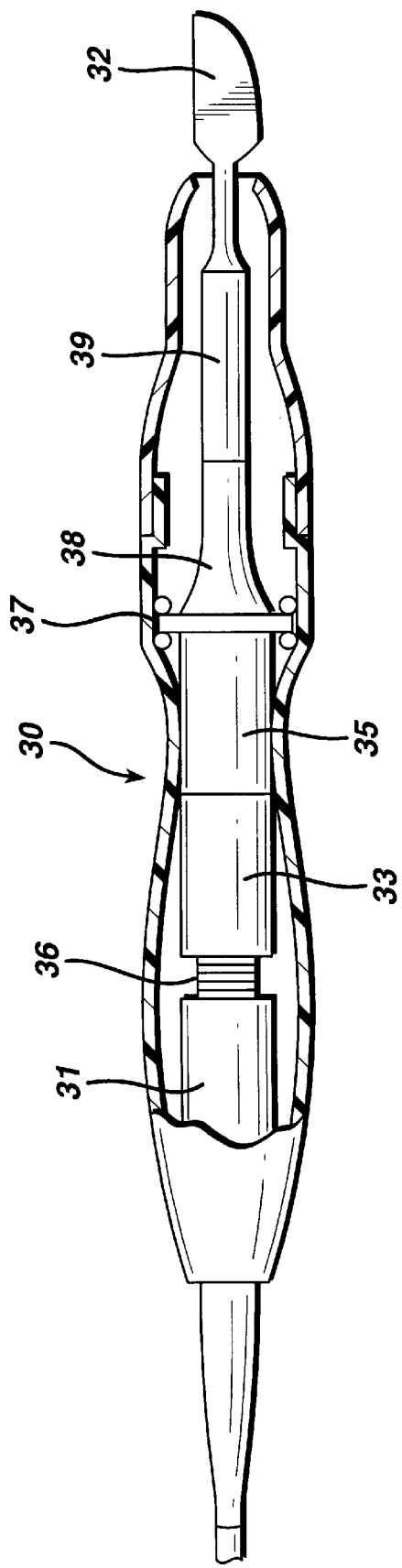
FIG. 2 is a schematic view of a cross section through the ultrasonic scalpel hand piece of the system of FIG. 1.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven with a maximum current at the transducers' resonant frequency. However, the current providing the maximum motion will vary with each hand piece and is a valve stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 3A:
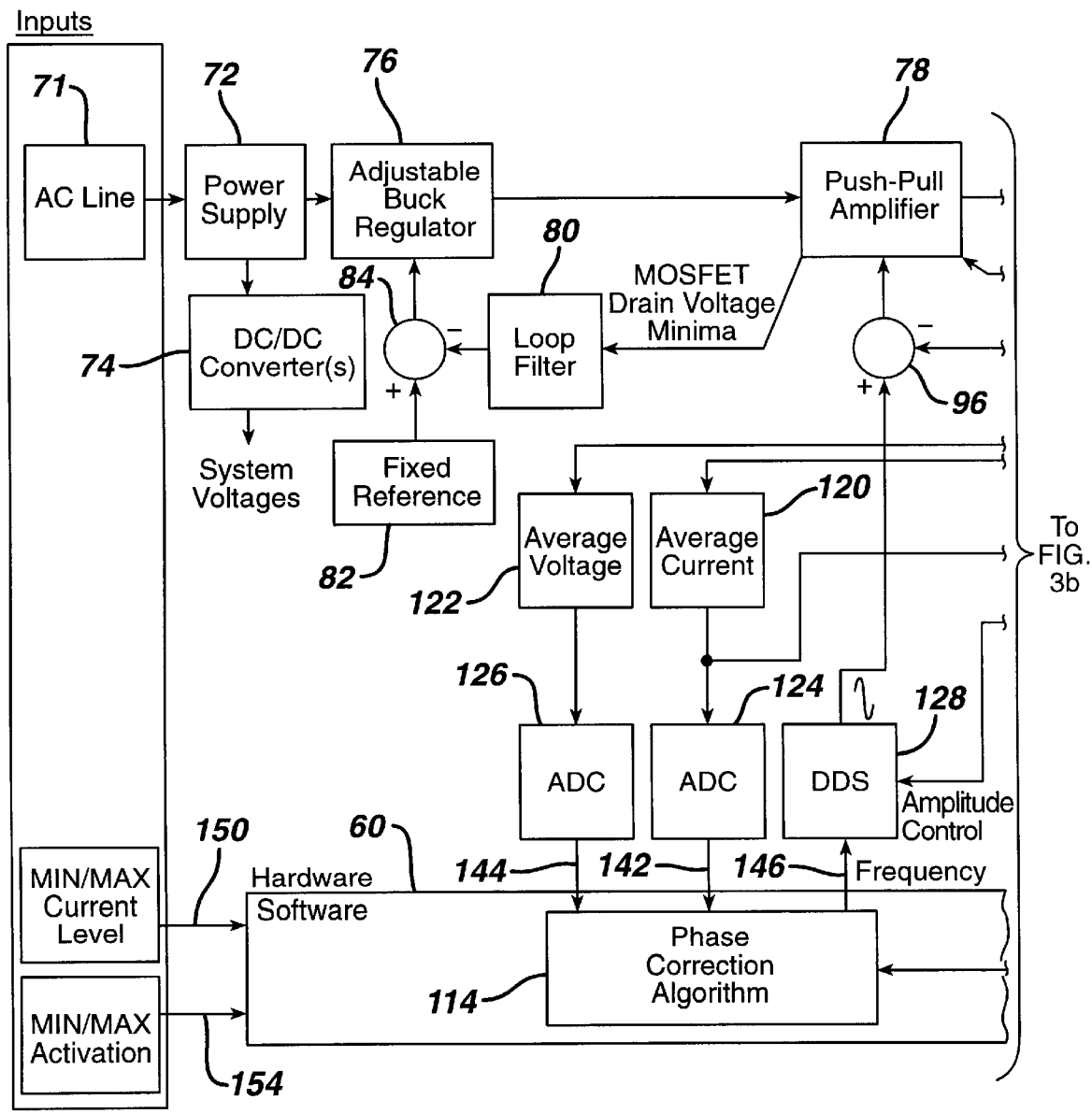
FIGS. 3(a) and 3(b) are block diagrams illustrating an ultrasonic generator for implementing the method of the present invention.
Figure 3B:
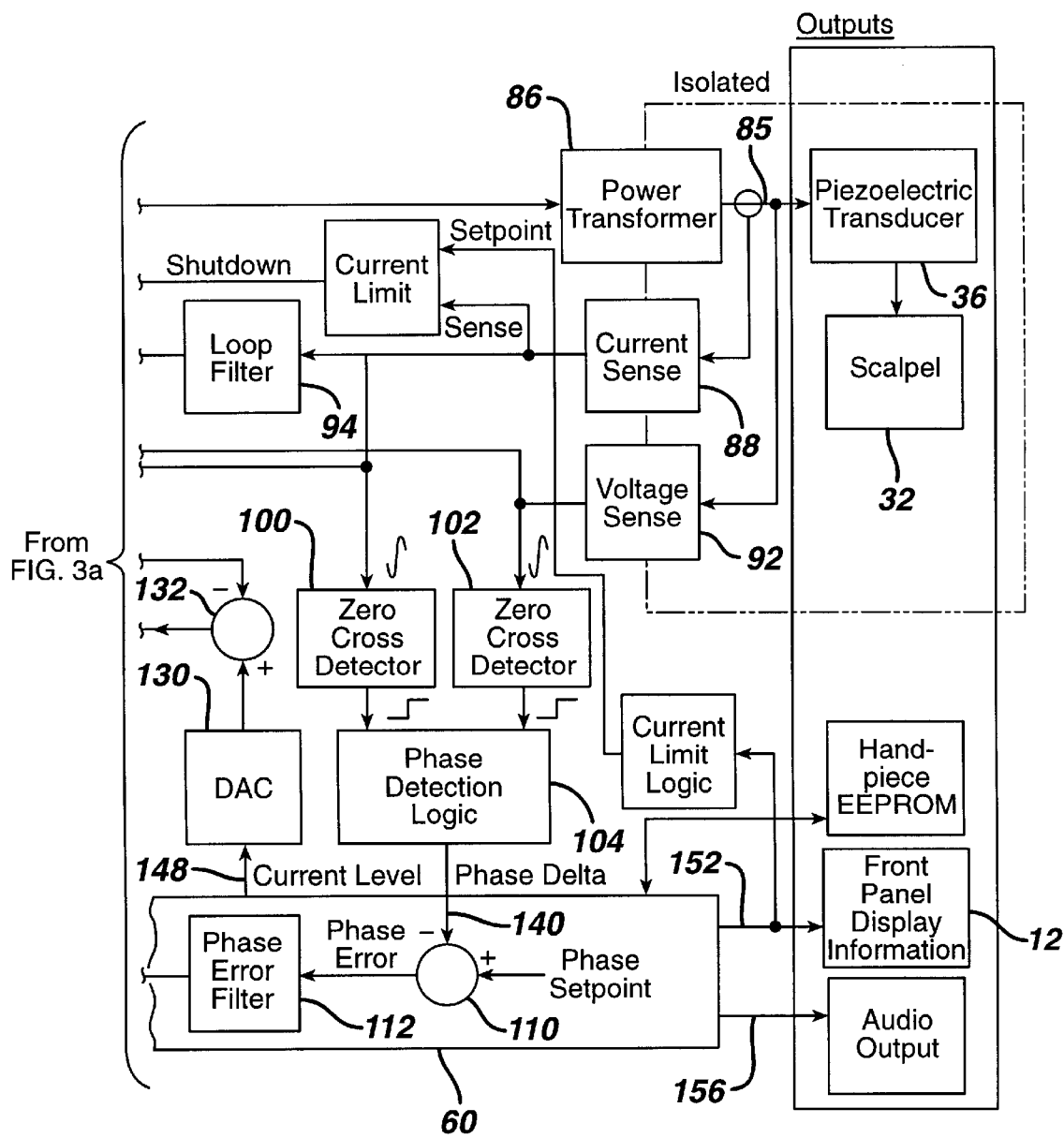

The system which creates the ultrasonic electrical signal for driving the transducer in the hand piece is illustrated in FIGS. 3(a) and 3(b). This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the hand piece/blade.

For example, under the control of a program stored in the DSP or microprocessor 60, such as a phase correction algorithm, the frequency during startup can be set to a particular value within a range, e.g., 20 kHz to 70 kHz. In the preferred embodiment, the frequency during startup is set to 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3(b)) to the console front panel display 12.

To actually cause the surgical blade to vibrate, the user activates the foot switch 40 or the hand piece switch 34. This activation puts a signal on line 154 in FIG. 3(a). This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

Figure 5A:
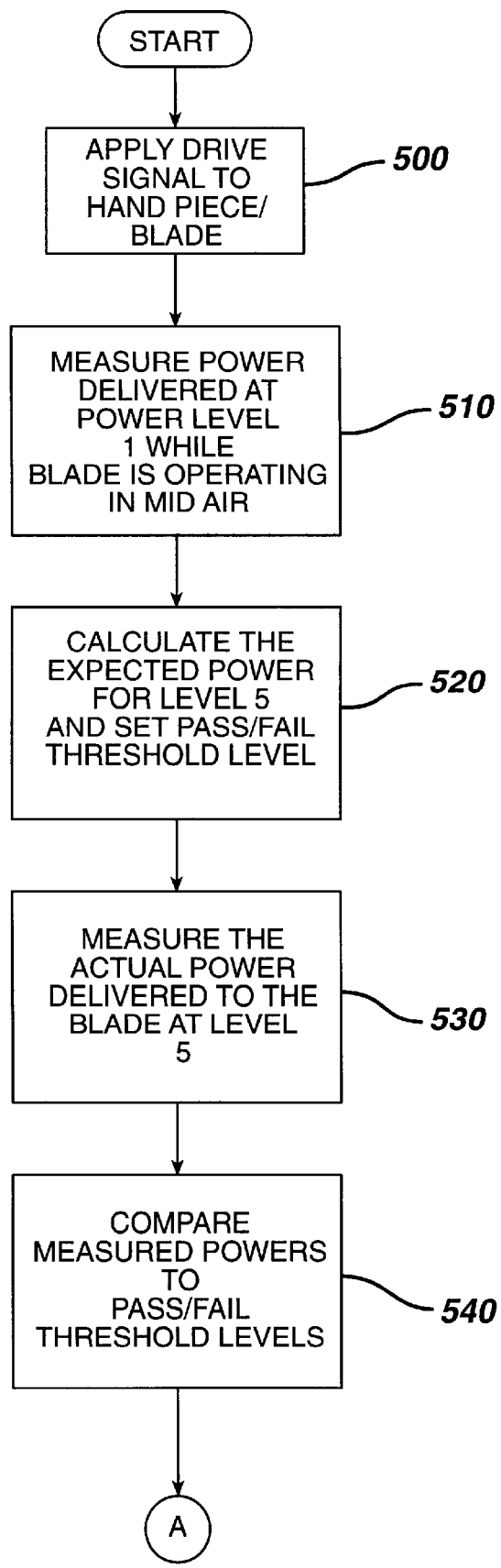
FIGS. 5(a) and 5(b) are flowcharts illustrating an embodiment of the method of the invention.
Figure 5B:
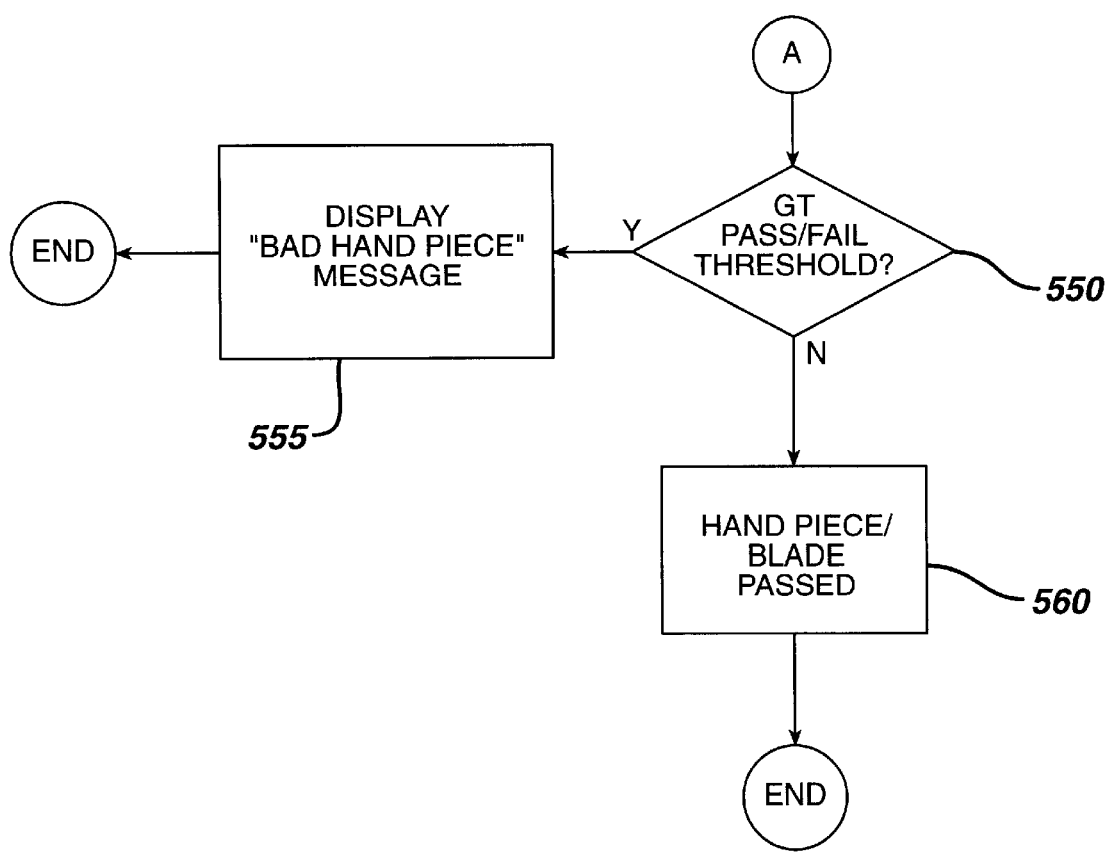

FIGS. 5(a) and 5(b) are flowcharts illustrating an embodiment of the invention. When a good transducer and blade are driven in free standing air, the impedance measured by the generator is independent of the drive current which corresponds to the specific power level in use, and the Power-Level vs. Power Delivered curve follows a quadratic relationship. Accordingly, upon measuring the power delivered at a single reference low power level setting, where no transverse vibrations can be triggered due to the low power level/drive current, the expected power delivered at other power levels may be extrapolated from the measured single reference low power level. This mathematical relationship holds true regardless of the type of blade being utilized with the hand piece. For purposes herein, the term power includes power and any of its components, including voltage, impedance, and current. Power also entails any other component that varies as a function of power, such as the temperature of the transducer.

Typical maximum power levels, which are used by the ultrasonic generator to drive the hand piece/blade, are shown in FIG. 4. Hand piece and blade combinations exhibiting transverse behavior at level 5 do not exhibit transverse mode behavior at power levels 1 or 2, and very rarely exhibits transverse mode behavior at power level 3. A hand piece/blade combination will occasionally exhibit transverse mode behavior at power level 4. Transverse behavior is indicated when the power into a hand piece/blade combination for a given load (in this case, while the blade is operating free standing) is higher than expected for the particular power level being applied to the blade.

Figure 9:
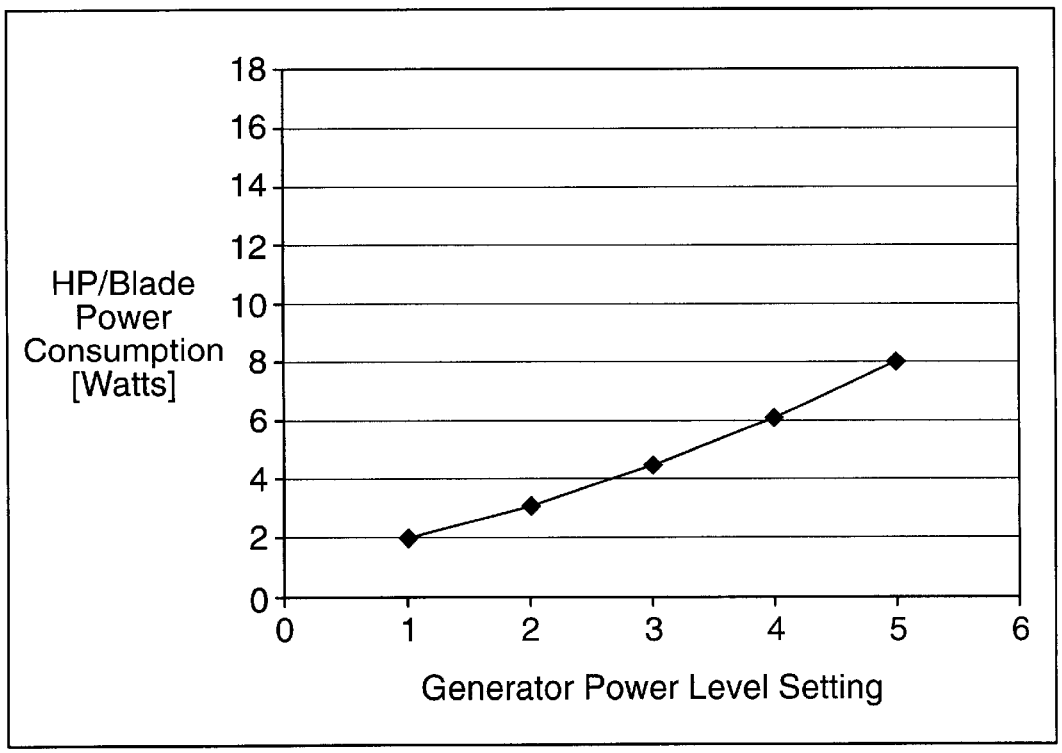
FIG. 9 is an illustration of a plot of transducer/blade power consumption at various generator power level settings when transverse vibrations are not present in the hand piece/blade.

Each power level is associated with a specific current at which the generator drives the hand piece transducer, and regulates across load changes on the blade. If the transducer/blade does not exhibit transverse vibrations, an increase of the power level will not increase the transducer/blade impedance which is measured by the generator. In this case, the expected increase in power delivered to the transducer/blade follows a known relationship (i.e., the power delivered as a function of the drive current). This relationship is true in cases where the level of transducer/blade impedance measured by the generator is independent of the drive current associated with the power level setting of the generator (i.e., when transverse vibrations are not present). The mathematical relationship of the power delivered as a function of drive current level and transducer/blade impedance is a quadratic relationship, as shown in FIG. 9. In the preferred embodiment, the quadratic relationship is:

$$P_L = (I_L)^2 * Z,  \quad \text{Eq. 1}$$

where $P_L$ is the power delivered to the transducer/blade, $I_L$ is the current delivered to the transducer (preset for each of the five power levels), and Z is the real part of the impedance.

If the transducer/blade exhibit transverse vibrations, an increase in the power level will increase the transducer/blade impedance which is measured by the generator. As a result, when transverse vibrations exist, the actual power delivered to the transducer/blade will exceed the expected power. Generally, transverse vibrations are rarely present at low power levels. This permits the performance of a reference power consumption measurement at a low power level setting to establish pass/fail power consumption levels for a high power level setting. The reference power level measurement is a necessary measurement, because the transducer/blade impedance measured by the generator is dependant upon the blade used. An accurate indicator of the presence of transverse mode vibrations is when the power consumption is greater than the expected threshold at high power levels (see FIG. 10).

Accordingly, under the control of the program stored in the DSP or microprocessor 60 shown in FIGS. 3(*a*) and 3(*b*), the method of the invention is implemented by using the ultrasonic generator to excite the hand piece/blade while it is being held in mid air, as indicated in step 500. While the blade is still being held in mid air, the power delivered to the hand piece/blade is measured at power level 1, as indicated in step 510. Using the measured power delivered to the hand piece/blade at level 1, the expected power for power level 5 is calculated, and a pass/fail threshold is set for power level 5 based on the expected power, as indicated in step 520. The pass/fail thresholds are set at a fixed percent above the calculated expected powers which are measured when transverse vibrations are not present in the hand piece/blade. In the preferred embodiment, the threshold is set at approximately 10% above the expected measured power.

The actual power deliver to the hand piece/blade at power level 5 is measured, as indicated in step 530. Next, the actual measured power is compared to the pass/fail threshold for power level 5, as indicated in step 540. If the actual measured power is greater than the respective pass/fail threshold (step 550), then operation of the generator is inhibited, a "Transverse Mode Vibrations Present in Hand Piece/Blade" error code is stored in the generator and a "Bad Hand Piece" message is displayed on the LCD of the console, as indicated in step 555. On the other hand, if the none of the actual measured powers are greater than the respective pass/fail threshold, then the hand piece/blade is good since it does not contain transverse mode vibrations, as indicated in step 560.

In order to obtain the impedance measurements and phase measurements, the DSP 60 and the other circuit elements of FIGS. 3(*a*) and 3(*b*) are used. In particular, push-pull amplifier 78 delivers the ultrasonic signal to a power transformer 86, which in turn delivers the signal over a line 85 in cable 26 to the piezoelectric transducers 36 in the hand piece. The current in line 85 and the voltage on that line are detected by current sense circuit 88 and voltage sense circuit 92. The current and voltage sense signals are sent to average voltage circuit 122 and average current circuit 120, respectively, which take the average values of these signals. The average voltage is converted by analog-to-digital converter (ADC) 126 into a digital code that is input to DSP 60. Likewise, the current average signal is converted by analog-to-digital converter (ADC) 124 into a digital code that is input to DSP 60. In the DSP the ratio of voltage to current is calculated on an ongoing basis to give the present impedance values as the frequency is changed. A significant change in impedance occurs as resonance is approached.

The signals from current sense 88 and voltage sense 92 are also applied to respective zero crossing detectors 100, 102. These produce a pulse whenever the respective signals cross zero. The pulse from detector 100 is applied to phase detection logic 104, which can include a counter that is started by that signal. The pulse from detector 102 is likewise applied to logic circuit 104 and can be used to stop the counter. As a result, the count which is reached by the counter is a digital code on line 104, which represents the difference in phase between the current and voltage. The size of this phase difference is also an indication of resonance. These signals can be used as part of a phase lock loop that cause the generator frequency to lock onto resonance, e.g., by comparing the phase delta to a phase set point in the DSP in order to generate a frequency signal to a direct digital synthesis (DDS) circuit 128 that drives the push-pull amplifier 78.

Further, the impedance and phase values can be used as indicated above in a diagnositic phase of operation to detect if the blade is loose. In such a case the DSP does not seek to establish phase lock at resonance, but rather drives the hand piece at particular frequencies and measures the impedance and phase to determine if the blade is tight.

Figure 6A:
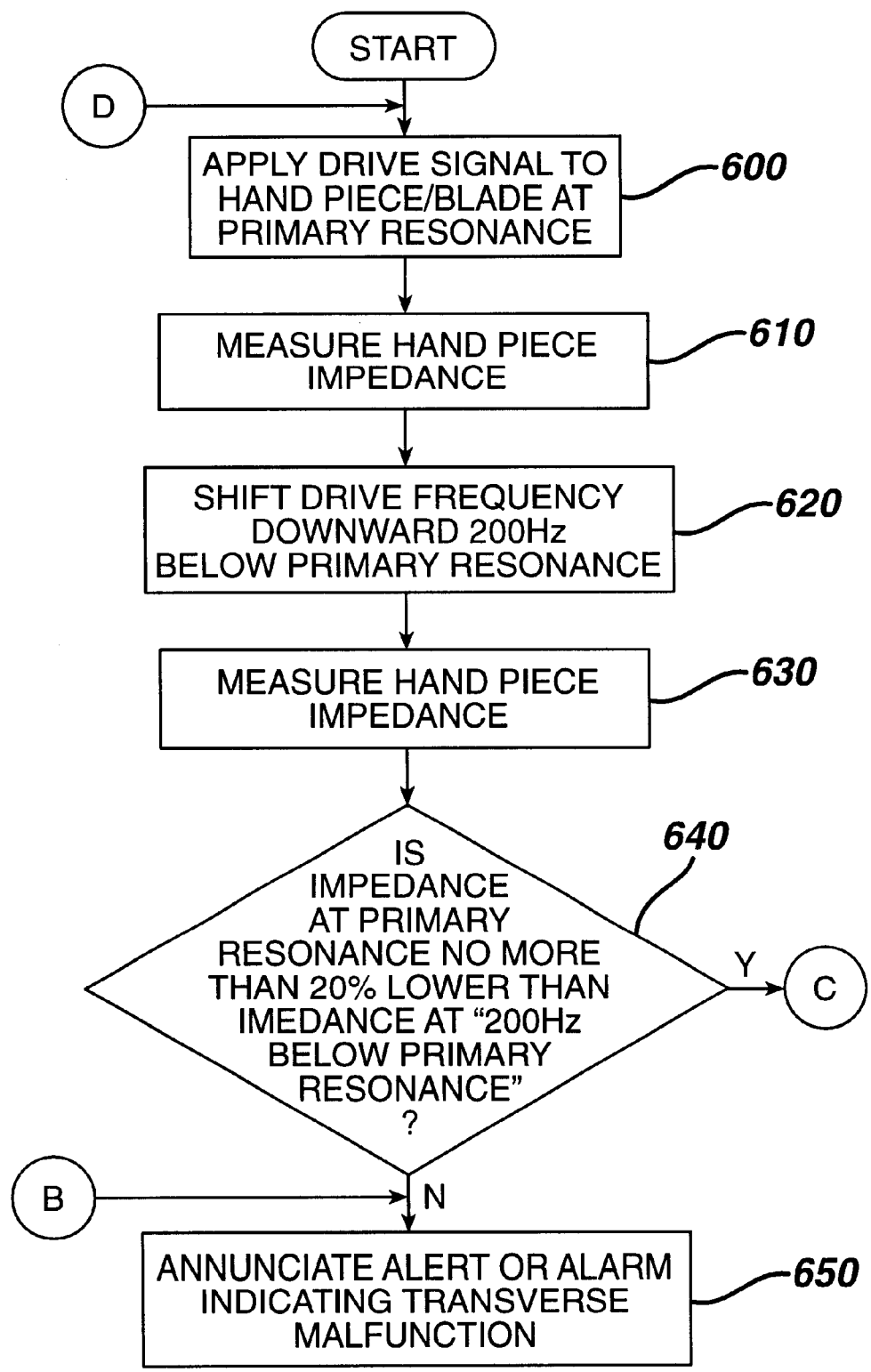
FIGS. 6(a) and 6(b) are flowcharts illustrating an embodiment of the invention.
Figure 6B:
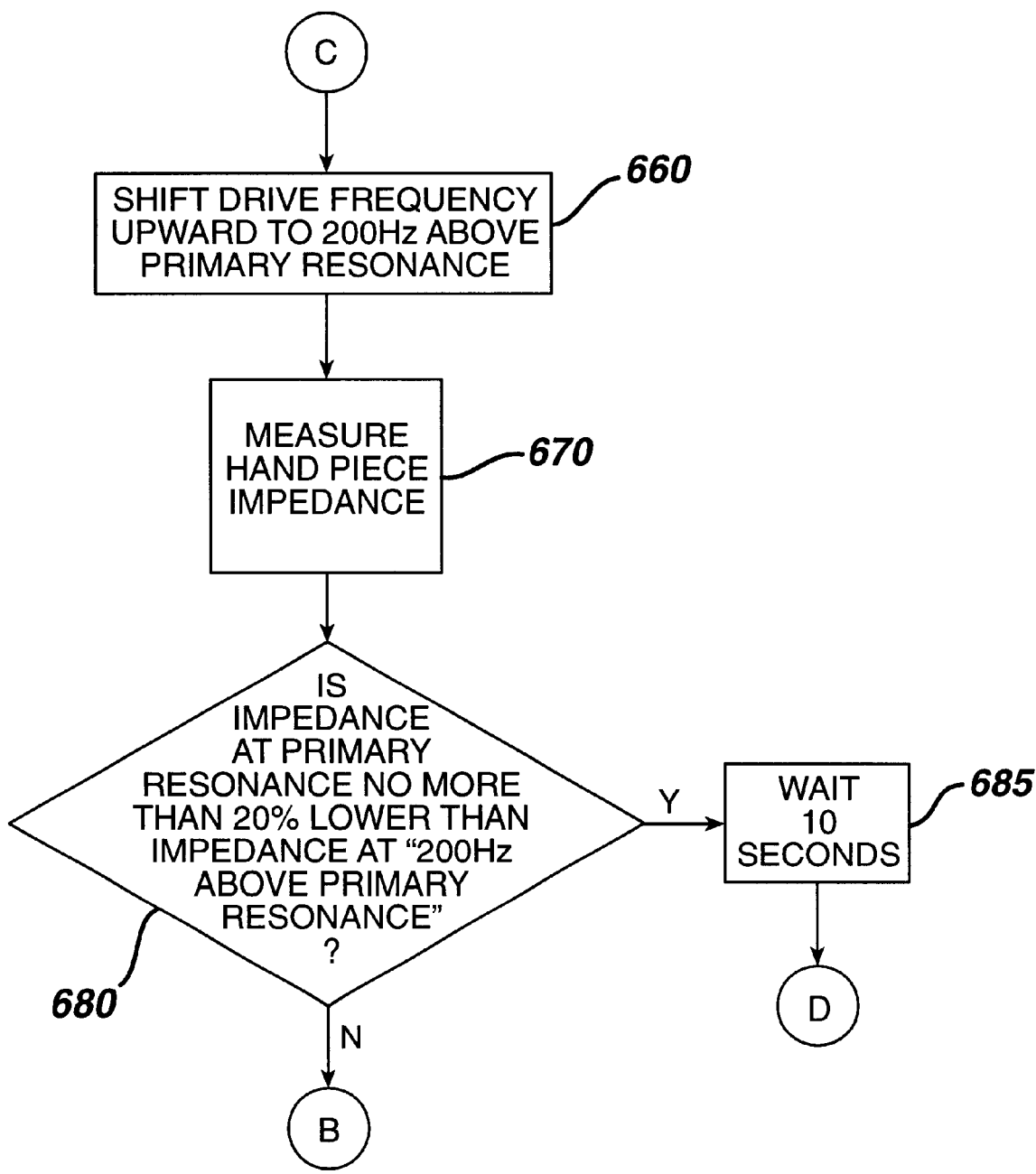

FIGS. 6(*a*) and 6(*b*) are flow charts illustrating another embodiment of the invention. When a good transducer and blade are driven in midair or in tissue, the Frequency vs. Power-Delivered Curve follows a known relationship. Accordingly, upon measuring the impedance of the hand piece at three nearby frequencies (i.e., the primary resonance and slightly off-resonance to above and below the primary resonance), the expected impedance of the hand piece at other frequencies may be extrapolated from these prior measurements. Generally, such a relative relationship exists for a variety of blades and shears.

One benefit of utilizing such a frequency-shift to detect transverse resonance is the test can be performed while the blade is in tissue. The shift away from the primary resonance is very brief. As a result, the tissue load does not appreciably change during the momentary shift. Thus, the effects of tissue loading do not substantially influence the resonance frequencies and resulting capability to detect transverse modes. As a result, the diagnostic procedure can be performed while the system is in use, particularly at level 5 or level 4 where problems with heat generated by transverse modes are most likely to occur. The method of the invention can be performed periodically, such as every 10 seconds, while the generator is driving the hand piece/bade, during a user-initiated diagnostic and/or at other desired times, such as while the blade is being held in mid air or is in contact with tissue.

Periodically during use, such as during use at level 5 and/or level 4 which are more likely to stimulate and evoke a substantial transverse motion than during use at level 1, level 2 or level 3, the drive frequency is moved slightly away from the primary resonance for a brief period of time. In the preferred embodiment, the primary resonance is changed by approximately 50 to 500 hertz and the brief period of time is approximately 10 msec to 0.5 seconds. If the output power, output current or other parameter substantially shifts (i.e., the impedance increases appreciably, for example), then a transverse frequency is being driven or is close to being driven via stimulation from the primary frequency. For example, the generator can be driving the blade at the primary intended resonance and if a transverse mode resonance is close by, it is highly likely to be more stimulated by the slight shift in frequency towards that transverse mode resonance. Even a slight shift from the primary resonance causes considerable energy coupling to any close transverse mode resonance. The difference in impedance and/or power change when shifting from primary resonance to the slightly off resonance frequency is measured and compare to an expected impedance change for a properly operating non-transverse condition system. If a transverse mode resonance is or is about to become problematic, the slightly off resonance impedance changes will be different for a good vs. a problematic transverse mode hand piece. In the preferred embodiment, the changes measured are power level, current level, impedance, phase, or the like.

The comparison to a properly operating non-transverse mode condition system may be based on established pass/fail criteria and/or by performing a measurement when first using a particular blade to obtain a baseline measurement which is reliable. For example, the nearest transverse frequencies are determined by sweeping the frequency of the drive signal in the general vicinity of the expected primary resonance and identifying any resonances which exist. Such a sweep is performed when a blade is first installed on the hand piece. Thereafter, the generator periodically drives the hand piece/blade at these particular transverse frequencies to monitor any shift which occurs. Alternatively, if the type of blade attached to the hand piece is known, the established pass/fail thresholds for that blade can be more specifically defined without the need to sweep the actual blade prior to use.

Under control of the program stored in the DSP or microprocessor 60 shown in FIGS. 3(*a*) and 3(*b*), the method of the invention is implemented by using the ultrasonic driver unit to drive the hand piece/blade at a primary resonance frequency, as indicated in step 600. In the preferred embodiment, the primary resonance frequency is 55 Khz.

The power delivered to the hand piece is measured, as indicated in step 610. The primary drive frequency is shifted downward by approximately 200 Hz, as indicated in step 620. A measurement of the hand piece impedance is performed, as indicated in step 630. A check is performed to determine whether the hand piece impedance at the primary resonance is no more than 20% lower than the hand piece impedance measured at 200 Hz below the primary frequency, as indicated in step 640.

If the hand piece impedance at the primary resonance is more than 20% lower than the impedance measured at 200 Hz below the primary frequency, then an alert or alarm is generated to indicate that a transverse malfunction is present, as indicated in step 650. If the hand piece impedance at the primary resonance is no more than 20% lower than the hand piece impedance at 200 Hz below the primary frequency, the drive frequency is shifted upward by approximately 200 Hz above the primary resonance frequency, as indicated in step 660. The hand piece impedance is measured, as indicated in step 670. A check is performed to determine whether the hand piece impedance at the primary resonance is no more than 20% lower than the hand piece impedance measured at 200 Hz above the primary frequency, as indicated in step 680.

If the measured hand piece impedance at the primary resonance is no more than 20% lower than hand piece impedance measured at 200 Hz above the primary frequency, then a pause is initiated (step 685), and a return to step 600 occurs. In the preferred embodiment, the pause is for approximately 10 seconds. If, on the other hand, the hand piece impedance at the primary resonance is more than 20% lower than the hand piece impedance measured at 200 Hz above the primary frequency, then a return to step 650 occurs, where the alert or alarm is generated to indicate that a transverse malfunction is present within the hand piece/blade. Alternatively, the power delivered to the hand piece may be measured, using a constant drive. When transverse mode vibrations are present, the power delivered to the hand piece will be appreciably greater.

FIGS. 7 is a flow chart illustrating an alternative embodiment of the invention. When a good transducer and blade are driven while being held in free standing air, the Power-Delivered vs. Drive Current Level curve and Hand Piece/Blade Impedance vs. Drive Current Level curve follow a known mathematical relationship. In the case of the Hand Piece/Blade Impedance vs. Drive Current curve, the mathematical relationship is an approximately straight line (i.e., the impedance measured by the generator is independent of the drive current level), and in the case of the Power-Delivered vs. Drive Current Level curve the mathematical relationship is quadratic, as shown in FIG. 9. These mathematical relationships hold true irrespective of the type of blade being utilized with the hand piece.

Figure 10:
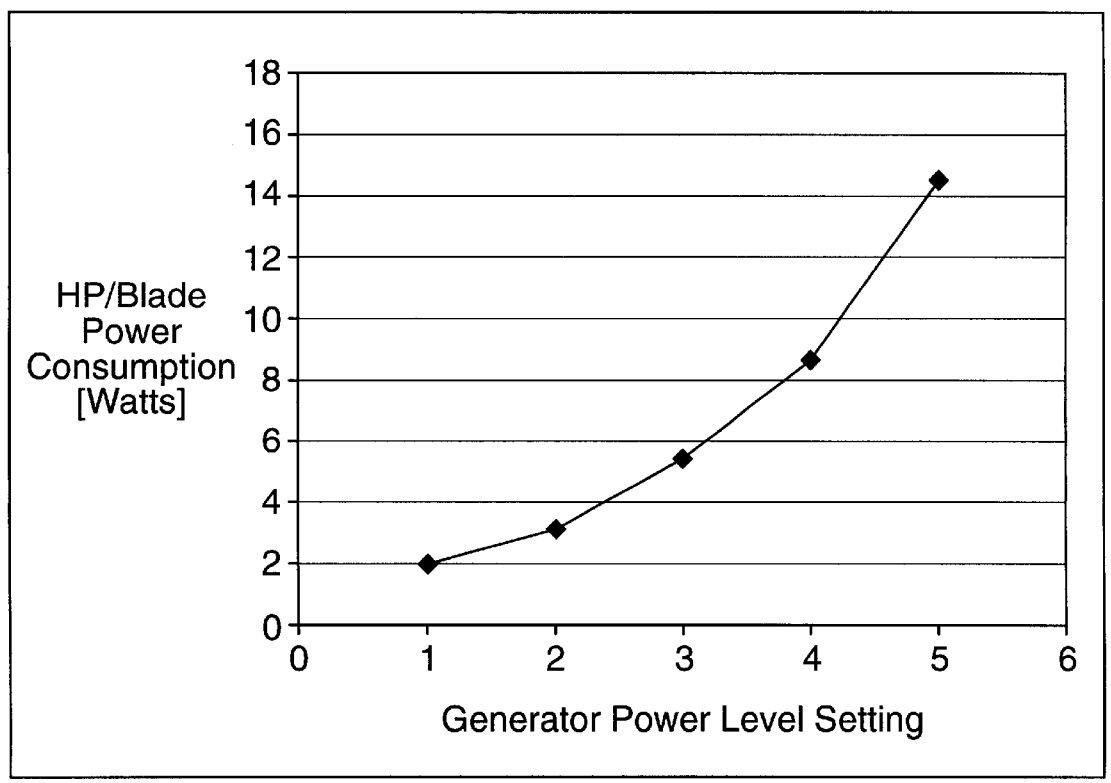
FIG. 10 is an illustration of a plot of transducer/blade power consumption at various generator power level settings when transverse vibrations are present in the hand piece/blade.
Figure 11:
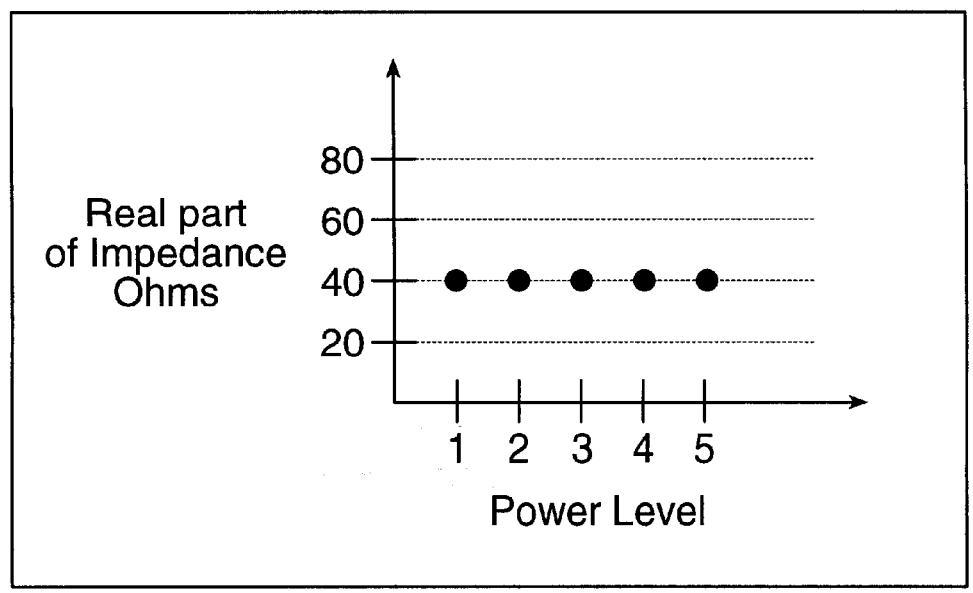
FIG. 11 is an illustration of a plot of transducer/blade impedance at various generator power level settings when transverse vibrations are not present in the hand piece/blade.
Figure 12:
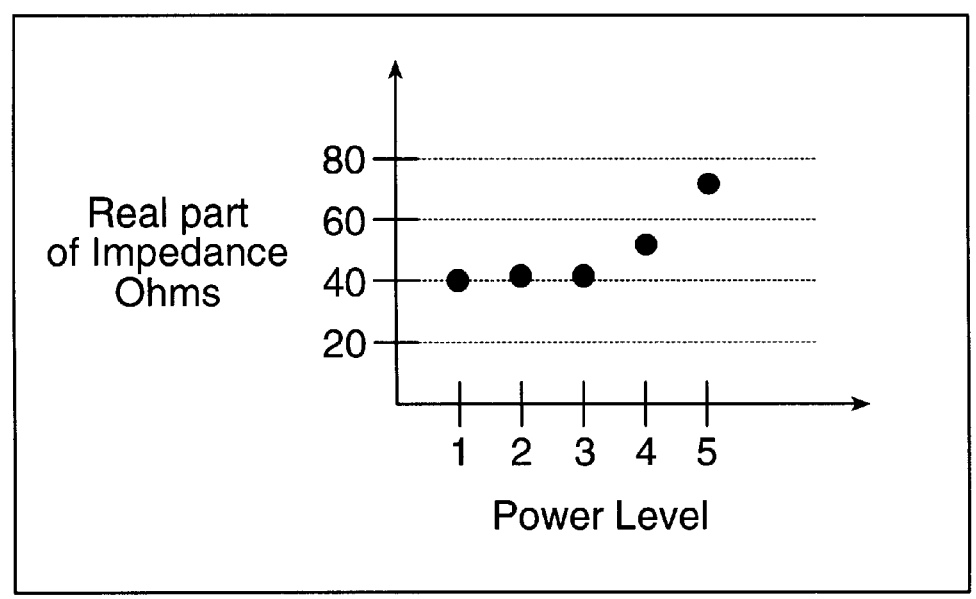
FIG. 12 is an illustration of a plot of transducer/blade impedance at various generator power level settings when transverse vibrations are present in the hand piece/blade.

In the presence of transverse behavior, the Power-Delivered vs. drive current level curve and the Hand Piece/Blade Impedance vs. Drive Current Level curve fail to follow the known mathematical relationships. Transverse behavior is indicated when the power into the transducer and blade combination for a given load (in this case, while the blade is operating free standing or in mid air) is higher than expected for the particular power level which is being applied to the blade (i.e. higher impedance and higher power), as shown in FIG. 10.

Accordingly, under control of the program stored in the DSP or microprocessor 60 shown in FIGS. 3(*a*) and 3(*b*), while the blade is held free standing in mid air, the method of the invention is implemented by using the ultrasonic driver unit to sweep the drive current level applied to the hand piece/blade from the minimum drive current level to the maximum drive current level, as indicated in step 700. In the preferred embodiment, the minimum current level is 100 mA RMS and the maximum current level is 425 mA RMS.

During the current sweep, the transducer voltage level and current drive level are monitored and stored in non-volatile memory located in the generator, as indicated in step 710. Using the stored voltage and current data, the power delivered to the transducer is calculated, and the Power-Delivered vs. Drive Current Level and Hand Piece/Blade Impedance vs. Drive Current Level response curves are generated, as indicated in step 720.

Using the generated response curves, an extrapolation is performed to determine whether the Hand Piece/Blade exhibits transverse mode vibrations which may create heat, as indicated in step 730. The extrapolation comprises checking the generated response curves to determine whether they represent a relationship which is equivalent to a straight line (e.g., for impedance comparisons) or a relationship which is quadratic (e.g., for power comparisons). In the preferred embodiment, the quadratic relationship is in accordance with Eq. 1. If transverse behavior is present (step 740), i.e., the curves fail to follow the expected mathematical 10 relationships (i.e., the relationships are exceeded), operation of the generator is inhibited, a "Transverse Mode Vibrations Present in Hand Piece/Blade" error code is stored in the generator, and a "Bad Hand Piece" message is displayed on the LCD of the console, as indicated in step 745. On the other hand, if the curves are consistent with the expected mathematical relationships, then the hand piece/blade is good since it does not contain transverse mode vibrations, as indicated in step 750.

Figure 8A:
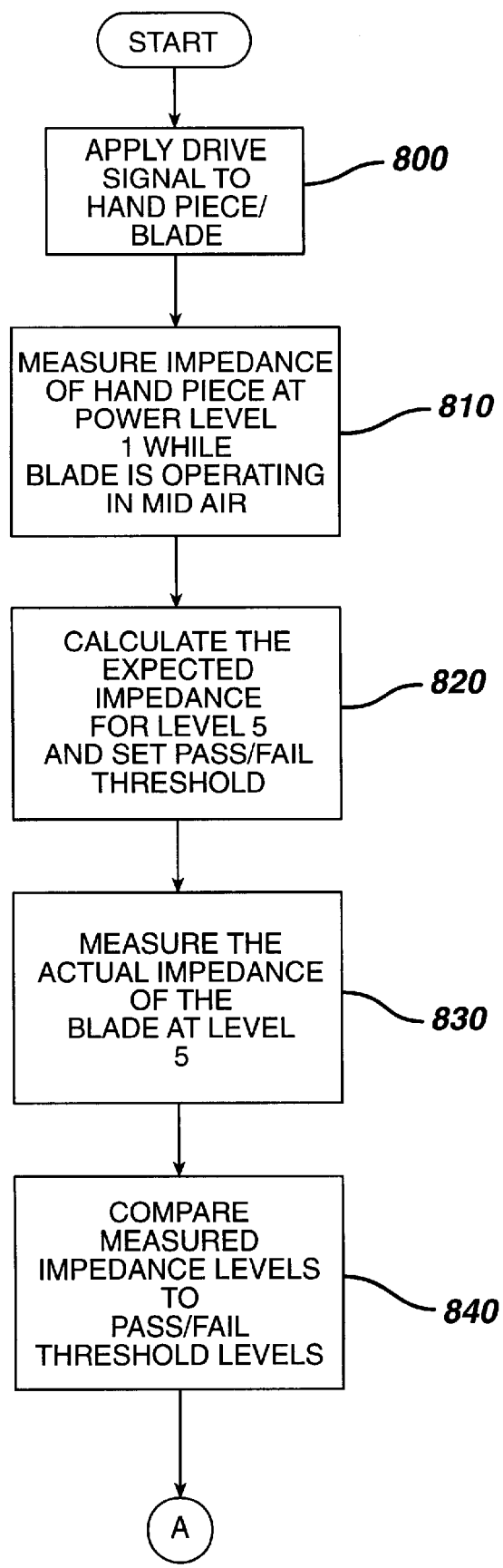
FIGS. 8(a) and 8(b) are flowcharts illustrating a preferred embodiment of the invention.
Figure 8B:
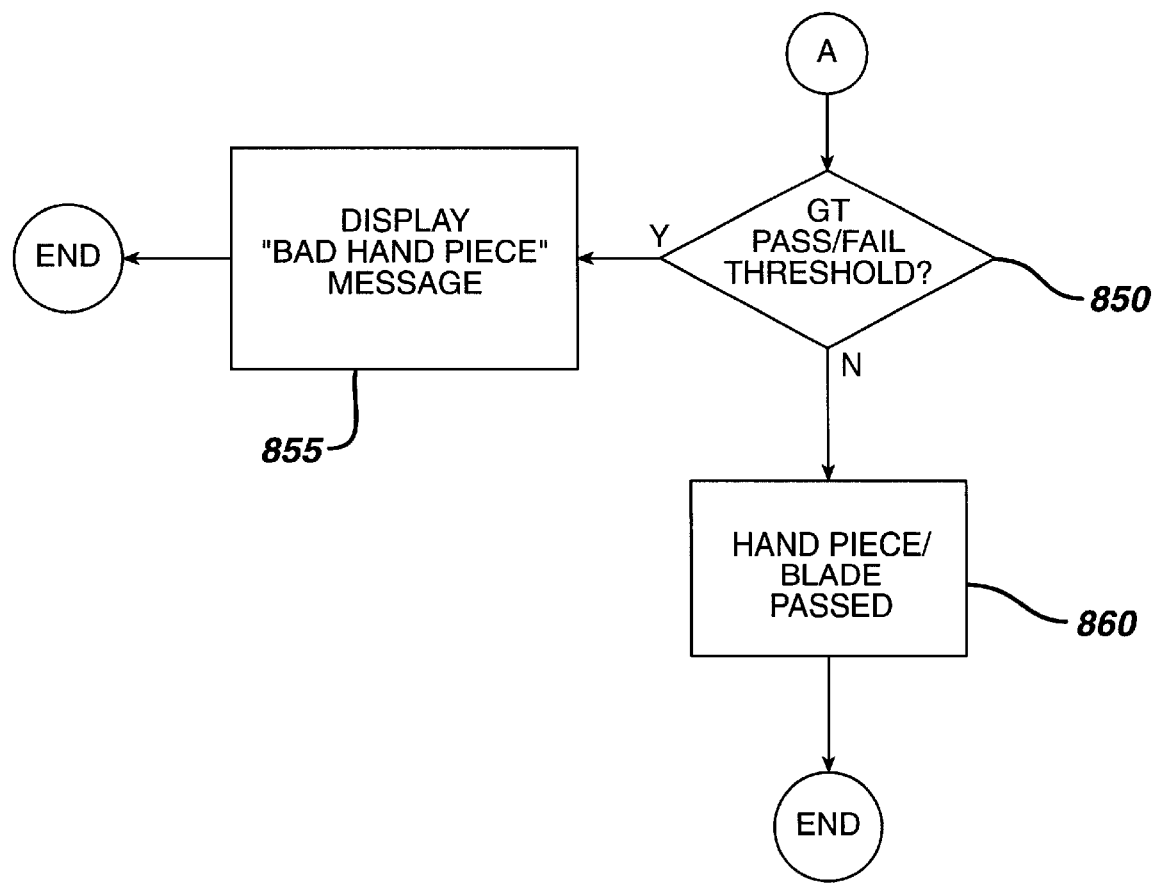

FIGS. 8(*a*) and 8(*b*) are flowcharts illustrating a preferred embodiment of the invention. Under the control of the program stored in the DSP or microprocessor 60 shown in FIGS. 3(*a*) and 3(*b*), the method of the invention is implemented by using the ultrasonic generator to excite the hand piece/blade while it is being held in mid air, as indicated in step 800. While the blade is still being held in mid air, the impedance of the hand piece/blade is measured at power level 1, as indicated in step 810. Using the measured impedance of the hand piece/blade at level 1, the expected impedance for power level 5 is calculated, and a pass/fail threshold is set for power level 5 based on the expected impedance, as indicated in step 820. The pass/fail thresholds are set at a fixed percent above the calculated expected power which is measured when transverse vibrations are not present in the hand piece/blade. In the preferred embodiment, the threshold is set at approximately 10% above the expected measured impedance.

The actual impedance of the hand piece/blade at power level 5 is measured, as indicated in step 830. Next, the actual measured impedance is compared to the pass/fail threshold for power level 5, as indicated in step 840. If the actual measured impedance is greater than the respective pass/fail threshold (step 850), then operation of the generator is inhibited, a "Transverse Mode Vibrations Present in Hand Piece/Blade" error code is stored in the generator and a "Bad Hand Piece" message is displayed on the LCD of the console, as indicated in step 855. On the other hand, if the none of the actual measured impedances are greater than the respective pass/fail threshold, then the hand piece/blade is good since it does not contain transverse mode vibrations, as indicated in step 860.

In a further embodiment, whether the circuit is being driving in a transverse state, or whether transverse modes are about to occur is determined. Specifically, periodically during use of the system, preferably when operating at level 5, which is more apt to stimulate substantial transverse motion, the drive frequency is briefly changed such that it is slightly off resonance (i.e., above/below the primary/main resonance). Here, the blade will still be substantially driven at its main resonance frequency. If a transverse mode vibration is nearby, it is highly likely to be more stimulated by the slight shift in drive frequency. The intent is to not extend too far from the primary resonance peak (approximately 100 Hz to 500 Hz, for example) such that there is still a considerable amount of energy coupling to the primary resonance and also to any nearby transverse mode vibrations.

Next, a check of the difference in impedance and/or power when moving from the primary resonance frequency to the slightly off resonance frequency is performed. For example, a comparison of a measured power change to an expected power change for a properly operating non-transverse non-problematic system is performed. If a transverse mode is, or is about to become, problematic, the slightly off resonance changes will be different for a good vs. a problematic hand piece/blade. The slightly off resonance check is brief and relatively transparent to the user. In the preferred embodiment, the comparison of on resonance measurements and slightly off resonance measurements is performed between the power, the impedance, the phase shift, or another variable. The comparison is between at least one of an absolute value, a delta, a rate of change and/or a $2^{nd}$ derivative.

If transverse mode vibrations are detected, the transverse activity can be attenuated by shifting the primary resonance drive frequency such that it is shifted slightly off center of the resonance frequency. In the preferred embodiment, the frequency is shifted in a direction opposite to transverse sensitivity. The check for transverse activity is repeated, and if the attenuations fail to halt the transverse behavior, operation of the ultrasonic system is terminated and/or the user us alerted to the undesirable condition. The present embodiment provides a means to safely avoid overheating the blade, damaging the blade, or overheating the hand piece.

In an alternative embodiment, a Multiple Level Drive Power vs. Power Delivered relationship and/or a Multiple Level Drive Power vs. Impedance relationship is used to detect or predict potential transverse mode problems, along with an "over-drive" of the hand piece at one or several power drive levels beyond the normal range of power levels used. These "over-drive" power levels are particularly effective at rapidly identifying problematic or potentially problematic transverse mode conditions.

In another embodiment, the power delivered to the hand piece is measured at multiple frequencies while a high power drive signal is applied to the hand piece. Alternatively, an "over-drive" is used. Here, three frequencies, i.e., a first frequency, a second frequency and a third frequency, are measured in close proximity to each other. The first frequency is the primary resonance frequency, otherwise referred to as the main or intended resonance frequency of the hand piece/blade. The second frequency is slightly below the first frequency. The third frequency is slightly above the first frequency.

Generally, power level 5 is the maximum power which is output during use. This power is the largest intended level for performing a measurement of power delivered to the hand piece. However, in accordance with the present embodiment, a power (i.e., a current) beyond Level 5 is briefly applied (100 msec, for example) to the hand piece/blade. This briefly applied power has a minimal impact upon tissue, but inputs substantially more power into the hand piece to more effectively engage neighboring transverse resonant frequencies and more effectively identify potential transverse mode problems. As a result, the "overdrive" provides a greater ability to identify potentially problematic transverse modes, since this intentional excessive drive has a greater ability to rapidly evoke a transverse resonance response that would not otherwise be seen, or be adequately prominent, if driving at the normal maximum range associated with power level 5. Alternatively, multiple "overdrives" can be utilized to quickly identify non-linearities between power levels, and thereby reveal potential transverse mode conditions and reduce the need to perform measurements at lower operating levels.

Alternatively, the hand piece/blade is momentarily driven at one "overdrive" power level which is approximately 10% above the maximum of power level 5 when in use. If transverse modes are present or imminent, such an "overdrive" quickly reveals a dramatically higher power or different impedance than normally expected at level 5. In an embodiment, comparisons are based on tables of commonly expected pass/fail limits which are indexed to blade types, such as automatic blade identification or a manually entered blade type.

In another embodiment of the invention, the presence of transverse mode vibrations is determined by monitoring both the transducer drive voltage and the transducer drive current to detect whether the Hand Piece/Blade Impedance vs. Frequency curve or the Power-Delivered vs. Frequency curve deviate from the expected curve which is relatively steep. In accordance with the present embodiment, while the blade is being held in midair or in tissue, the frequency is swept from a minimum frequency to a maximum frequency. During the frequency sweep, the transducer voltage level and current drive level are monitored and stored in memory located in the generator or in the blade. Using the stored voltage and current data, the power delivered to the hand piece is calculated, and the Power-Delivered vs. Frequency and the Hand piece/blade Impedance vs. Frequency response curves are generated. Using the generated response curves, an extrapolation is performed to determine whether the Hand piece/blade exhibits transverse mode vibrations or is in a marginal state and therefore about to exhibit transverse mode behavior. Such transverse modes can create heat at undesired locations in the system which can be hazardous. If a transverse mode resonance is determined to exist, an alarm or alert is generated by the generator to permit the user to halt system use or take other appropriate steps. In alternative embodiments, the generator automatically stops driving the hand piece.

In another embodiment, the presence of transverse mode vibration is detected by calculating ratios of measured impedances at multiple power levels and determining the presence of transverse vibrations based on the calculated ratios. In preferred embodiments, the impedance at level 5 is measured and the impedance at level 1 is measured. Next, the ratio of the measured power levels is compared to a predetermined threshold to determine whether transverse vibrations are present. In preferred embodiments, the predetermined threshold is 1.6.

In a further embodiment of the invention, predictive measures are used to avoid or mitigate the onset of transverse resonances. Often, transverse resonances are stimulated by frequencies near or at the primary resonance. The frequency "gap" between such resonances can shrink during use due to blade heating, which can eventually result in inadvertently driving the hand piece/blade at the transverse frequency. By periodically monitoring the nearest transverse resonance frequency, the gap between such resonant frequencies can be determined and the relative potential for inadvertently driving the hand piece/blade at transverse frequencies can be measured and used to predict potential transverse mode problems. For example, higher drive levels tend to heat up the blade faster, and hence more quickly reduce the gap. This predictive information is used to then halt driving of the transducer, alert a user that a potential transverse problem may be about to occur or alter the primary drive frequency to bias it slightly away from the ideal resonance at a frequency further away from the transverse frequency. The size of the gap, the rate of change of the gap and/or the $2^{nd}$ derivative of the gap can be used to provide predictive information about the relative potential and/or existence of transverse modes.

In preferred embodiments of the invention, the current (i.e., "power level") is related to power by the relationship $P=I^2 * Z$, where the current I is rms amperes, and Z is the real part of the impedance. Hence, at a first low level $P_1=* Z_1$. At a second high level $P_2=I_2^2 * Z_2$. In cases where Z does not increase (or decrease), then $P_2/P_1=(I_2/I_1)^2$. Accordingly, in the case where actual measurements of $P_1$ and $P_2$ reveal that $P_2/P_1>(I_2/I_1)^2$, then transverse vibrations are present in the hand piece.

Using the method of the present invention, an indication of whether a hand piece which failed the power level tests will exhibit transverse vibrational modes is provided. Moreover, as a consequence of the mathematical relationship holding true irrespective of the type of blade, the method can be used with any hand piece/blade combination. In addition, the method also ensures safe operation of the hand piece by preventing overheating of the blade, thus avoiding damage to the blade or injury to an individual using the hand piece.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for detecting transverse vibrations in an ultrasonic hand piece, comprising the steps of:
    applying a drive signal to an ultrasonic hand piece using an ultrasonic generator;
    measuring an electrical characteristic delivered to the hand piece/blade at a first electrical characteristic level while the hand piece/blade is held in midair;
    calculating an expected electrical characteristic using the first electrical characteristic level;
    setting a pass/fail threshold level for an actual measured electrical characteristic based on the expected electrical characteristic;
    measuring the actual electrical characteristic delivered to the hand piece/blade;
    comparing the measured actual electrical characteristic to the pass/fail threshold;
    if the measured actual electrical characteristic is less than the pass/fail threshold, displaying a first message on a liquid crystal display of the generator; and
    if the measured actual electrical characteristic is greater than the pass/fail threshold, displaying a second message on a liquid crystal display of the generator.

2. The method of claim 1, wherein the first message is a "Hand Piece/Blade Passed" message.

3. The method of claim 1, wherein the first electrical characteristic level is a power level.

4. The method of claim 3, wherein said calculating step comprises the step of:
    calculating the expected electrical characteristic for a level five setting.

5. The method of claim 4, wherein the electrical characteristic is power.

6. The method of claim 3, wherein the level 5 setting is approximately 425 ma RMS.

7. The method of claim 3, wherein the power level is approximately 100 ma RMS.

8. The method of claim 1, wherein said step of displaying a second message comprises the step of:
   storing a "Transverse Mode Vibrations Present in Hand Piece/Blade" error code in the generator; and
   displaying a "Bad Hand Piece" message on the liquid crystal display of the generator.

9. The method of claim 1, wherein the drive signal has a frequency of approximately 20 Khz to 70 KHz.

10. The method of claim 1, wherein the pass/fail threshold is approximately 10 percent of the expected electrical characteristic.

11. The method of claim 10, wherein the electrical characteristic is power.

12. A method for detecting transverse vibrations in an ultrasonic hand piece, comprising the steps of:
   sweeping a drive signal having a voltage and current applied to an ultrasonic hand piece/blade using an ultrasonic generator;
   monitoring and storing parameters applied to the hand piece/blade in non-volatile memory located in the ultrasonic generator;
   calculating an electrical characteristic delivered to the hand piece based on the stored voltages and stored currents;
   generating response curves based on the stored parameters;
   performing an extrapolation using the response curve to determine whether the hand piece/blade exhibits transverse modes;
   if the hand piece/blade exhibits transverse modes, displaying a message on a liquid crystal display of the generator.

13. The method of claim 12, wherein the message is a "Hand Piece/Blade Contains Transverse Mode Vibrations" message.

14. The method of claims 12, wherein said applying step comprises the step of:
   applying the drive signal from a minimum drive current level to a maximum drive current level.

15. The method of claim 14, wherein the minimum drive current level is approximately 100 ma RMS and the maximum drive current level is approximately 425 ma RMS.

16. The method of claim 12, wherein the response curves are at least one of a Power-Delivered vs. Drive Current Level curve and a Hand Piece/Blade impedance vs. Drive Current level curve.

17. The method of claim 12, wherein the extrapolation comprises the step of:
   checking the generated response curves to determine whether any curve represents at least one of a straight line and a relationship which is quadratic.

18. The method of claim 12, wherein the electrical characteristic is power.

19. The method of claim 12, wherein the parameters are voltages and currents.

* * * * *